United States Patent
Skalitzky et al.

(10) Patent No.: US 6,722,578 B2
(45) Date of Patent: Apr. 20, 2004

(54) APPARATUS FOR DISPENSING VOLATILE MATERIALS

(75) Inventors: Michael J. Skalitzky, Kenosha, WI (US); Chad D. Holland, Racine, WI (US)

(73) Assignee: S.C. Johnson & Son, Inc., Racine, WI (US)

(*) Notice: Subject to any disclaimer, the term of this patent is extended or adjusted under 35 U.S.C. 154(b) by 250 days.

(21) Appl. No.: 10/094,685

(22) Filed: Mar. 11, 2002

(65) Prior Publication Data

US 2003/0168521 A1 Sep. 11, 2003

(51) Int. Cl.[7] .............................. A24F 25/00; A61L 9/04
(52) U.S. Cl. .............................. 239/57; 239/53; 239/54; 239/55; 239/56
(58) Field of Search ........................ 239/57, 34, 35, 239/47, 55, 60, 53, 54, 56; 392/390, 386; 219/544, 541, 542, 543

(56) References Cited

U.S. PATENT DOCUMENTS

| | | |
|---|---|---|
| 4,145,001 A | 3/1979 | Weyenberg et al. |
| 4,157,787 A | 6/1979 | Schwartz |
| 4,328,181 A | 5/1982 | Anders et al. |
| 4,439,415 A | 3/1984 | Hennart et al. |
| 4,583,686 A | 4/1986 | Martens et al. |
| 4,595,612 A * | 6/1986 | Tavss et al. ............... 222/92 |
| 4,839,144 A | 6/1989 | Martin |
| 4,849,606 A | 7/1989 | Martens, III et al. |
| 4,921,636 A | 5/1990 | Traas |
| 5,439,100 A | 8/1995 | Gordon et al. |
| 5,518,790 A | 5/1996 | Huber et al. ............... 428/35.2 |
| 5,645,845 A | 7/1997 | Neumann et al. |
| 5,765,751 A | 6/1998 | Joshi |
| 5,788,155 A | 8/1998 | Martin et al. |
| 5,885,701 A | 3/1999 | Berman et al. |
| 5,904,028 A * | 5/1999 | Fujiura et al. ............... 53/431 |
| 6,031,967 A | 2/2000 | Flashinski et al. |
| 6,085,026 A | 7/2000 | Hammons et al. ......... 392/390 |
| 6,154,607 A | 11/2000 | Flashinski et al. |
| 6,447,795 B2 * | 9/2002 | Kalder et al. ............... 424/411 |

FOREIGN PATENT DOCUMENTS

| | | |
|---|---|---|
| DE | 42 39 025 A1 | 5/1994 |
| EP | 0 321 729 A2 | 6/1989 |
| GB | 2 302 507 A | 1/1997 |

OTHER PUBLICATIONS

A fuyi Vape box side, undated, admitted prior art, depicting a fuyi Vape heater.

* cited by examiner

Primary Examiner—Davis D Hwu

(57) ABSTRACT

A dispenser with a lid laminate providing controlled release of a volatile material contained in a tray is disclosed. The lid includes a vapor impermeable, removable outer laminate and a vapor permeable inner layer covering an open side of the tray. The outer laminate includes layers of polyethylene terephthalate (PET) and aluminum foil removably adhered to the inner layer of biaxially-oriented polypropylene (OPP) by an ethylene acrylic acid copolymer. Bottom and side walls of the tray are constructed of a metal/polymer pressure-formed colored tray laminate impermeable to the vapors and volatile material. The tray has a peripheral lip with an outer surface of cast polypropylene to which the vapor permeable inner layer of the lid is heat sealed.

14 Claims, 2 Drawing Sheets

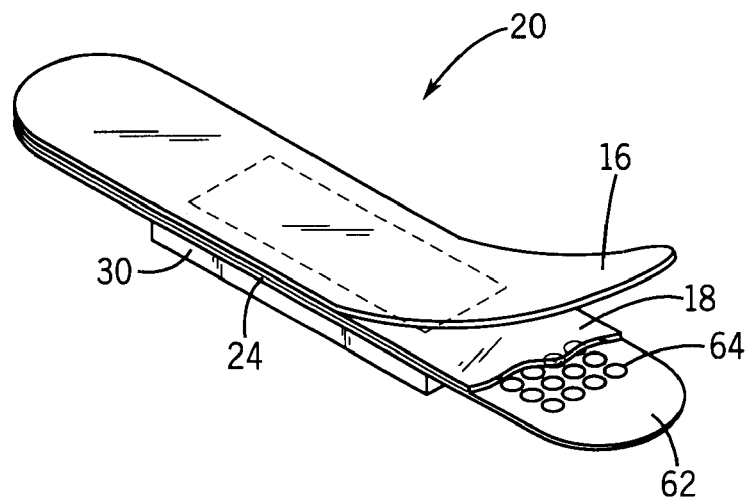
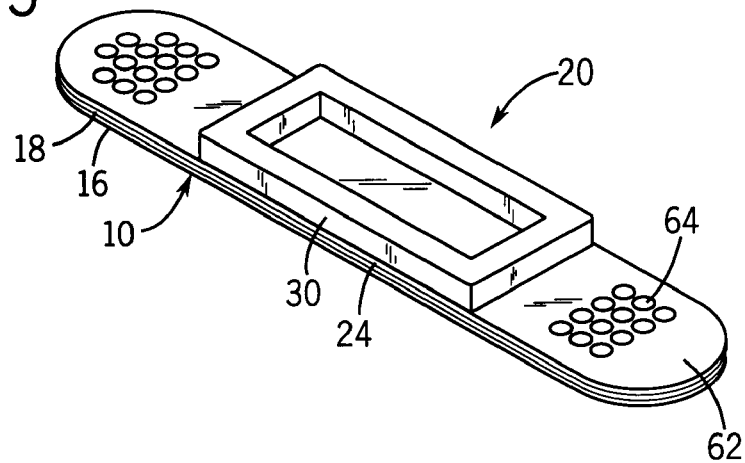
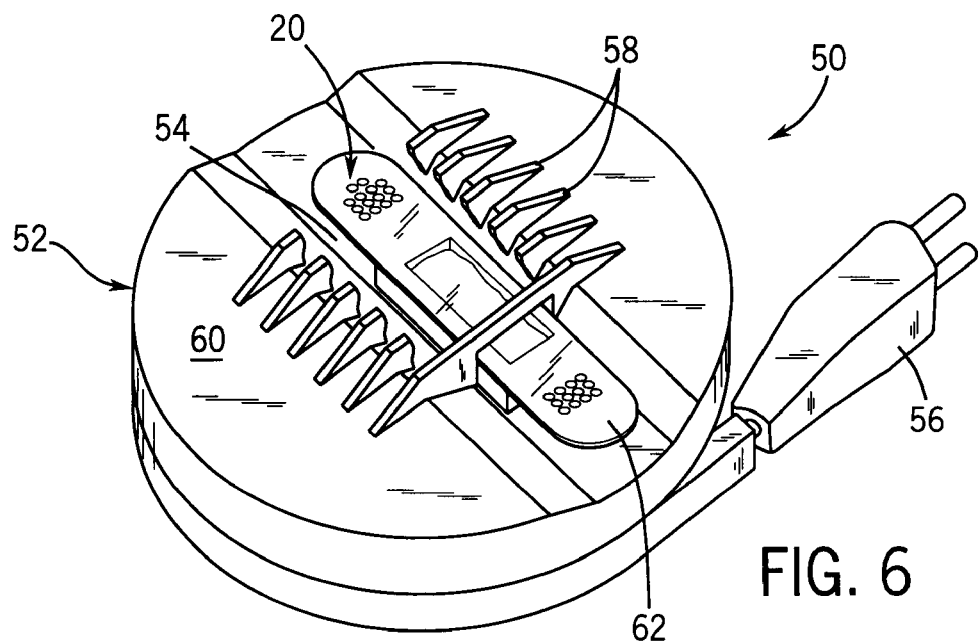

APPARATUS FOR DISPENSING VOLATILE MATERIALS

CROSS-REFERENCE TO RELATED APPLICATIONS

Not applicable

STATEMENT OF FEDERALLY SPONSORED RESEARCH/DEVELOPMENT

Not applicable

BACKGROUND OF THE INVENTION

The invention relates to devices for dispensing volatile materials. More specifically, the invention relates to a dispenser that permits the controlled release of volatile materials.

Ether and alcohol-based compounds are commonly used as carriers to distribute air-treating compounds into the atmosphere. For example, when combined with fragrances and/or deodorizing compounds these compounds are useful to reduce or eliminate offensive odors and to provide a long-lasting pleasant odor. When combined with bactericides, insecticides, and insect repellants, for example, these compounds are useful indoors and outdoors in combating unwanted insects and germs. A variety of packages have been used to contain these materials and permit the controlled dispensing of them as vapors into the atmosphere.

It is known in the art to impregnate a solid porous mat with a volatile material, or to place a volatile material in a pan-like metal structure. These mats and pans have been placed on heaters to cause the volatile material to vaporize into the atmosphere. One type of heater used for this purpose was sold by S.C. Johnson & Son, Inc. under the trademark FUYI VAPE. See also U.S. Pat. No. 4,439,415 for a general discussion of heater units used for this purpose. The disclosure of this patent, and of all other publications referred to herein, are incorporated by reference as if fully set forth.

U.S. Pat. No. 6,154,607, commonly owned with this application, also discloses a metal pan having a cavity that accommodates a substrate that is impregnated with a volatile material. The pan is placed on a heater which heats the pan, causing the release of the volatile material. The pan is covered with a permeable membrane that slows the release of the volatile material. However, the permeable member is not easily joined to the metal pan by heat sealing, a preferred, low-cost process that provides a vapor impermeable seal.

U.S. Pat. Nos. 4,145,001 and 5,885,701 describe heat sealed vapor impermeable packages with top and bottom substrates that are heat sealed around the periphery of the package containing the volatile material. The heat seal and the substrates are vapor impermeable. However, these packages are not designed to withstand the high temperatures of heaters and may have unsuitably high vapor-transmission rates. Moreover, the vapor permeable layers of these packages are not readily heat sealable to the metal pans or trays designed for use with such heaters.

Therefore, there is a need for an improved volatile material dispenser.

SUMMARY OF THE INVENTION

The invention provides a dispenser with a metallic tray and a vapor permeable lid. The tray contains the volatile material and has an open side with a cast polypropylene face surface. The lid is made of a biaxially oriented polypropylene (OPP) film and is attached to the face surface of the tray so as to cover the open side and permit release of vapors from the volatile material.

In one preferred form, the lid also includes a vapor impermeable outer cover laminate having a layer of polyethylene terephthalate and a foil layer releaseably joined to the OPP film of the lid. The foil layer is preferably adhered to the PET and the OPP by ethylene acrylic acid copolymer.

In another preferred form, the tray includes a bottom and side walls extending up from the perimeter of the bottom to a peripheral lip. After the dispenser is filled with the volatile material, the open end of the tray is preferably heat sealed with the vapor permeable lid and the vapor impermeable cover laminate. The heat sealing is preferably done from above the dispenser so as to limit heat exposure to the volatile. When the volatile material is to be dispensed, the vapor impermeable laminate is peeled back from the dispenser leaving the vapor permeable layer, which maintains the volatile material inside the dispenser and prevents the user from contacting the material while simultaneously permitting the vapor from the volatile material to be released into the surrounding atmosphere.

In another preferred form, the cast polypropylene face surface is joined to the tray by an adhesive laminate. The adhesive laminate includes a colored dye providing a visual indication of the exhaustion of the volatile material. The volatile material is contained within a gel that is transparent (when heated) as is the inner permeable layer of the film, thereby permitting the consumer to see the colored laminate when the dispenser is in use. As the volatile material is used up, the gel turns opaque (white) obscuring the view of the colored laminate and thereby providing a clearly visible end of use indication.

The dispenser may be used independently for dispensing a volatile material or it may be used in conjunction with an electrically-heated vapor-dispensing apparatus.

Other features will become apparent to those skilled in the art from a review of the following detailed description, taken in conjunction with the drawings and the appended claims. While the disclosed dispenser is susceptible of embodiments in various forms, described below are specific embodiments that are intended as illustrative (and not intended to limit the disclosure to the specific embodiments described herein).

BRIEF DESCRIPTION OF THE DRAWINGS

FIG. 4 is a perspective view of the volatile material dispenser shown in FIG. 1 with the vapor impermeable layer of the lid laminate partially removed;

FIG. 5 is a bottom perspective view of the volatile material dispenser of FIGS. 1 and 4; and FIG. 6 illustrates the dispenser of FIG. 1 with the vapor impermeable layer removed and inserted into an electrically-heated vapor-dispensing apparatus.

DETAILED DESCRIPTION OF THE PREFERRED EMBODIMENTS

Figure 1:
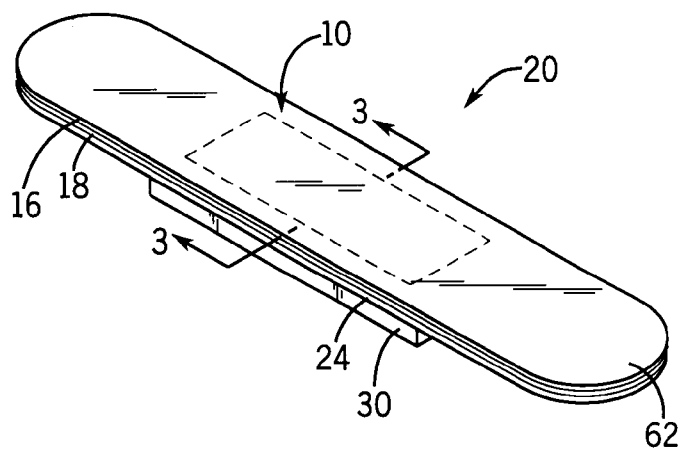
FIG. 1 is a top perspective view of a volatile material dispenser having a lid laminate covering a volatile-containing tray.
Figure 2:
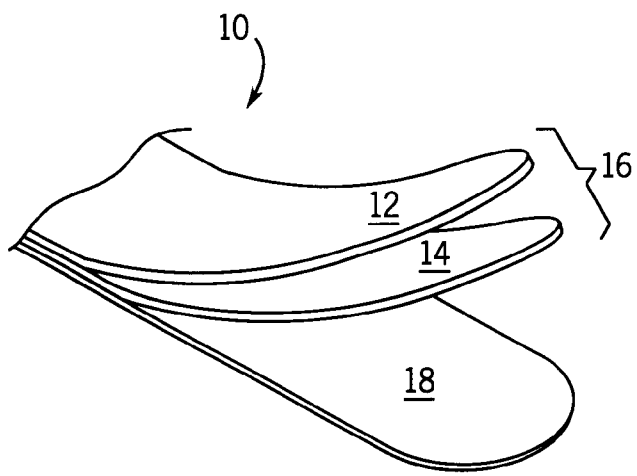
FIG. 2 is a perspective view of the lid laminate according to one embodiment of the disclosure.

Referring to FIG. 1, the invention provides a volatile material dispenser 20 having a lid laminate 10 and a tray 11.

The lid laminate 10 includes: (a) a first layer 12 comprising polyethylene terephthalate (PET); (b) a second layer 14 comprising an aluminum foil, which with the first layer forms a removable vapor impermeable outer laminate 16; and (c) a third layer comprising biaxially-oriented polypropylene (OPP) film forming a vapor permeable inner layer 18. In a preferred embodiment of the invention, the PET layer has a thickness of about 0.01 to about 0.0144 millimeters (mm), the foil layer has a thickness of about 0.01 to about 0.015 mm, and the OPP layer has a thickness of about 0.028 to about 0.042 mm.

Ethylene acrylic acid (EAA) copolymer acts as an adhesive joining the layers of the outer laminate 16 and joining the outer laminate 16 to the inner layer 18. More specifically, the EAA copolymer is used to securely bond one surface of the aluminum foil to the PET and releasably bond an opposite side surface of the aluminum foil to the OPP film.

The strength of the bond formed between EAA copolymer and the aluminum foil is greater than that of the bond formed between the EAA copolymer and the OPP film permitting a clean separation of the aluminum foil from the vapor permeable inner layer when the vapor impermeable outer laminate 16 is removed. The EAA copolymer can be formed by combining and co-extruding EAA with a linear low-density polyethylene.

Figure 3:
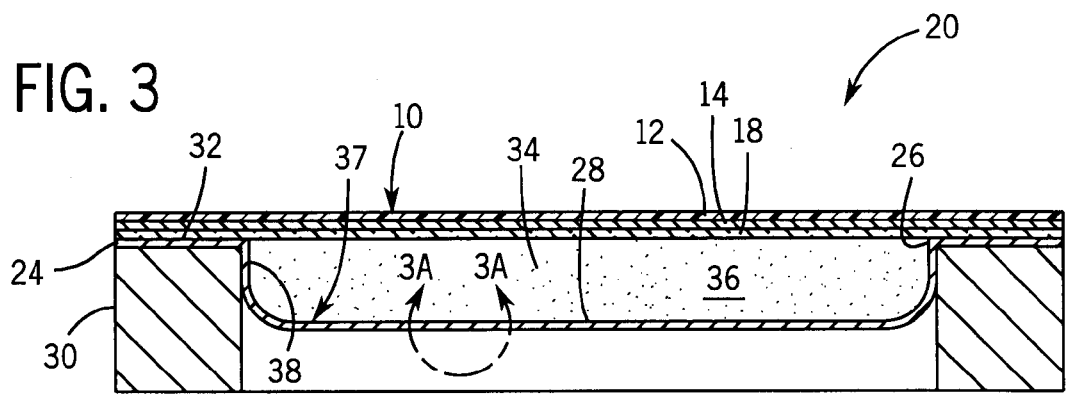
FIG. 3 is a sectional view taken substantially along line 3—3 of FIG. 1.
Figure 3A:
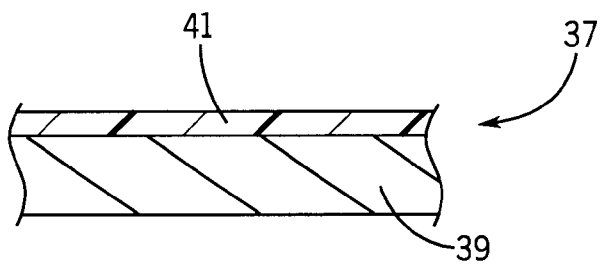
FIG. 3A is a partial enlarged sectional view of the dispenser tray as shown in FIG. 3.

FIGS. 1 and 3 illustrate the dispenser 20 having a tray-like structure with a peripheral flange or lip 24 surrounding an open side 26 and supported by outer side walls 30. The tray 11 forms an interior region 34 defined by a bottom wall 28 and interior side walls 38 that enclose the volatile material 36. The bottom wall 28, lip 24 and interior side walls 38 preferably are thermoformed or heat/pressure-formed from a metal/polymer laminate 37 as shown in FIG. 3A. The tray laminate 37 includes a layer of aluminum foil 39 that is over laminated with a cast polypropylene film 41 providing an upwardly facing outer face surface at the lip 24. The tray laminate 37 is impermeable to vapors of the volatile material enclosed by the substrate (dispenser). Accordingly, the tray laminate 37 provides low vapor transmission rates enabling prolonged storage of the dispenser prior to use by the end consumer.

Generally, any adhesive can be used to laminate the foil 39 to the cast polypropylene film 41. The adhesive can be colorless, however, in a preferred embodiment, the adhesive includes a colored dye, such as a blue-colored dye. Preferably the colored dye and the resultant colored tray laminate 37 are a different color than the volatile material so as to provide an "end-of-use" indicator.

Specifically, the tray laminate is colored and the volatile material 36 can comprise a clear gel in combination with the volatile functional material (i.e., insecticide, fragrance, etc.). As the volatile material 36 volatilizes, its appearance can change from a clear, substantially transparent appearance to an increasingly opaque appearance. In one embodiment, the gel turns white as the volatile functional material vaporizes. Further, the inner layer 18 of the lid 10 is substantially transparent. Thus, when new, the consumer can see the colored tray laminate 37 through the inner layer 18 and through the volatile material 36. As the volatile material 36 is used, it becomes increasingly opaque thereby blocking the consumer's view of the colored tray laminate 37. As a result, as the volatile material 36 is used up, the color is blocked by the increasingly opaque (e.g., white) appearance of the material 36 resulting in a clear end of use indication.

Use of such a colored tray is a marked improvement over dispensers in which dye is incorporated into the formulation of the volatile material where the dye could clog the pores of the vapor permeable membrane and thus impede the permeation of vapors. Further, the color change of the volatile material is more apparent in the present dispenser.

Once the dispenser 20 is filled with a volatile material, the opening 26 is sealed with the lid 10 described above. The lid 10 can be attached to the peripheral lip 32 of the dispenser 20 using any conventional means, such as an adhesive, heat sealing, crimping, or the like. Preferably, the vapor permeable inner layer 18 is attached by heat sealing means.

The tray laminate 37 is resilient to the high temperature heat that can be expected during heat sealing operations used to secure the lid to the dispenser. Moreover, the inner vapor permeable layer 18 of the lid 10 (made of a OPP film) is highly molecularly compatible with the cast polypropylene layer 41 of the tray laminate 37 providing highly consistent and impermeable seals. Moreover, the heat sealing operation can be performed from above the tray 11 (i.e., with the heat element closer to the lip 24 than the bottom wall 28), which shortens the dwell time and thus reduce unwanted heat exposure to the volatile material.

When the volatile material is to be dispensed, the vapor impermeable outer laminate 16 is peeled back from the dispenser leaving the vapor permeable inner layer 18. The inner layer 18 maintains the volatile material inside the dispenser and prevents the user from contacting the material while simultaneously permitting the vapor from the volatile material to be released into the surrounding atmosphere.

The dispenser 20 can be utilized independently in any conventional manner of utilizing an open ended container having a polymeric film. A preferred use is as a slow diffusion air-treating material dispenser 20, such as a fragrance dispenser, which is placed in an appropriate location after removal of the impermeable sealing layer(s) to permit the slow diffusion of the volatile material into the surrounding atmosphere.

Additionally, the dispenser 20 is particularly suitable for use as a single-use cartridge for an electrically-heated vapor-dispensing apparatus. When used with such an apparatus, the dispenser 20 preferably is made in the shape of a cartridge as shown in FIGS. 2–5 which complements the interior structure of the apparatus.

An example of such an apparatus is illustrated in FIG. 6. As shown in FIG. 6, the apparatus 50 comprises a body 52 having a slot 54 extending through the body 52 in which the dispenser 20 is insertable. The body 52 of the apparatus 50 preferably is injection molded and has an integral part thereof a heating element (not shown) and an electrical plug 56, which is inserted into an electric outlet during use of the apparatus 50.

When the heating apparatus 50 is used to generate a vapor, the vapor impermeable outer laminate 16 of the lid 10 is removed and the dispenser 20 is inserted into slot 54 of the apparatus 50. After the dispenser 20 is inserted into the heating apparatus 50, the electrical plug 56 of the apparatus 50 is inserted into an electric outlet (not shown). The interior of the apparatus 50 is heated thereby causing the material 36 contained in the dispenser 20 to be heated and diffused into the surrounding atmosphere through the vapor permeable inner layer 18 of the lid 10 and between the protective grids 58 (five of which are broken away in FIG. 6 for purposes of illustration) that are integrally formed with the top wall 60 of the apparatus 50.

Various modifications can be made to the dispenser 20. For example, when the dispenser 20 is used either independently or with a heating apparatus 50, two ends 62 of the peripheral lip 24 surrounding the opening 26 of the dispenser 20 can be extended in length as shown in FIGS. 3, 4 and 5. The extended portions 62 provide a gripping or holding areas for the user, which aid in preventing the rupture of the lid 10 by providing an alternate place for holding the dispenser 20.

When used with a heating apparatus 50, the extended portions 62 provide areas to hold during the insertion of the dispenser 20 into the apparatus 50. The extended portion 62 also can include one or more projections 64 protruding from at least one surface of the extended portions 62 in any form, such as lines, bulbs, the name or logo of the seller in raised outline, or the like, which provide for better gripping of the extended portion 62 of the lip 24. The projections 64 preferably are disposed on the undersides of the extended portions 62 if a fingerhold area is desired. These projections 64 can serve to aid in the separation of the vapor impermeable outer laminate 16 from the vapor permeable inner layer 18 of the lid 10 and from the extended portions 62 so that the user can more easily grasp an end of the film 10 and remove the vapor impermeable outer laminate 16 prior to use. The extended portions 62 also facilitate removal of the dispenser 20 from the heating apparatus 50.

As previously noted, while the dispenser can be filled with any desired material, it is particularly suited for use in holding a volatile material which is to be slowly diffused into the surrounding atmosphere, such as a fragrance. A fragrance can be relatively simple in composition, or can be a complex mixture of natural and/or synthetic chemical components. Most conventional fragrance materials are synthetic or naturally-derived volatile essential oils, such as, for example, oil of bergamot, bitter orange, lemon, mandarin, caraway, cedar leaf, clove leaf, cedar wood, geranium, lavender, orange, origanum, petitgrain, white cedar, patchouli, lavandin, neroli, rose absolute, and the like. Suitable natural botanical fragrances also can be employed, such as, those selected from the group consisting of eucalyptus, floral notes, jasmine-lavender, wintergreen, spearmint, wood notes, wormwood, echinacea, lemongrass, calendula, balsam, oleoresins, tea tree, ginseng, licorice, menthol. Synthetic types of fragrance compositions either alone or in combination with natural oils are described in U.S. Pat. Nos. 4,314,915; 4,411,829; and 4,434,306, which are incorporated herein by reference.

Other artificial liquid fragrances include geraniol, geranyl acetate, eugenol, isoeugenol, linalool, linalyl acetate, phenethyl alcohol, methyl ethyl ketone, methylionone, isobomyl acetate, and the like. Any other fragrances not specifically mentioned herein but having similar characteristics, configurations, and/or structures can be used with equal efficacy.

A liquid fragrance can be formed into a thixotropic gel by the addition of a conventional thickening agent, such as, for example, fumed silica of the type marketed under the CABOSIL trademark (Cabot Corporation), or other thickening agents known by those skilled in the art. The fragrance also can be in the form of a crystalline solid, which has the ability to sublime into the vapor phase at ambient temperatures.

A crystalline fragrance starting material can be selected from organic compounds which include, but are not limited to, vanillin, ethyl vanillin, coumarin, tonalid, calone, heliotropene, musk xylol, cedrol, musk ketone benzophenone, raspberry ketone, methyl naphthyl ketone beta, phenyl ethyl salicylate, veltol, maltol, maple lactone, proeugenol acetate, evemyl, and the like. This type of fragrance can contribute a long term air-treating capability to an air freshener dispenser device.

As one specific example, the dispenser can be used for dispensing an insect active. In one preferred such formulation, the volatile material includes a 97.98% of transfluthrin (94.4 technical grade), 2% Cabosil PTG and 0.02% fatty acid methyl ester (FAME). The Cabosil provides a gel consistency and serves as the opaque end of use indicator, as described above. The FAME acts as a diluent for the active ingredient. In particular, FAME is an inert substance that blends easily with the active to form a homogeneous fluid. FAME is chosen here because it has approximately the same vaporization rate as transfluthrin and can be used to adjust for differences in the purity or technical grade of transfluthrin, which can vary from one reaction batch to the next. This allows different purity actives to be used in mass production of the dispensers while maintaining the overall percentage of the active ingredient consistent.

The foregoing description is given for clearness of understanding only, and no unnecessary limitations should be understood therefrom, as modifications within the scope of the invention may be apparent to those skilled in the art.

INDUSTRIAL APPLICABILITY

The present disclosure provides a dispenser with an improved lid structure for providing secure closure during storage, and controlled release of a volatile during use.

We claim:

1. A volatile material dispenser, comprising:
    a metallic tray containing a volatile material and having an open side with a cast polypropylene face surface; and
    a lid having a vapor permeable layer made of a biaxially oriented polypropylene film attached to the face surface to cover the open side of the tray and permit release of vapors from the volatile material;
    wherein the lid also comprises a foil layer releaseably joined to the vapor permeable layer of the lid; and
    wherein the vapor permeable layer of the lid has been heat sealed to the tray.

2. The dispenser of claim 1, wherein the lid further includes a vapor impermeable cover laminate.

3. The dispenser of claim 2, wherein the cover laminate includes the aforesaid a foil layer releaseably joined to the vapor permeable layer of the lid.

4. The dispenser of claim 3, wherein the foil layer is adhered to the vapor permeable layer by ethylene acrylic acid copolymer.

5. The dispenser of claim 1, wherein the vapor permeable layer of the lid is heat sealed to the tray from above the tray.

6. The dispenser of claim 1, wherein the tray includes a bottom and side walls extending up from the perimeter of the bottom to a peripheral lip.

7. The dispenser of claim 1, wherein the vapor permeable layer of the lid is sealed to the peripheral lip.

8. The dispenser of claim 1, wherein the cast polypropylene face surface is joined to the tray by an adhesive laminate.

9. The dispenser of claim 1, wherein the volatile material includes an active ingredient and a diluent.

10. The dispenser of claim 9, wherein the active is transfluthrin and the diluent is fatty acid methyl ester.

11. A volatile material dispenser, comprising:
    a metallic tray containing a volatile material and having an open side with a cast polypropylene face surface; and a lid having a vapor permeable layer made of a biaxially oriented polypropylene film attached to the face surface to cover the open side of the tray and permit release of vapors from the volatile material;

wherein the lid further includes a vapor impermeable cover laminate;

wherein the cover laminate includes a foil layer releaseably joined to the vapor permeable layer of the lid;

wherein the foil layer is adhered to the vapor permeable layer by ethylene acrylic acid copolymer; and wherein the cover laminate further includes a layer of polyethylene terephthalate, wherein the foil layer is disposed between the biaxially oriented polypropylene face surface of the lid and the polyethylene terephthalate layer.

12. A volatile material dispenser, comprising:

a metallic tray containing a volatile material and having an open side with a cast polypropylene face surface; and a lid having a vapor permeable layer made of a biaxially oriented polypropylene film attached to the face surface to cover the open side of the tray and permit release of vapors from the volatile material;

wherein the vapor permeable layer of the lid is sealed to the peripheral lip; and wherein the adhesive laminate includes a colored dye providing a visual indication of the exhaustion of the volatile material.

13. A volatile material dispenser, comprising:

a metallic tray containing a volatile material and having an open side with a cast polypropylene face surface; and a lid having a vapor permeable layer made of a biaxially oriented polypropylene film attached to the face surface to cover the open side of the tray and permit release of vapors from the volatile material;

wherein the volatile material includes an active ingredient and a diluent;

wherein the active is transfluthrin and the diluent is fatty acid methyl ester; and wherein the volatile material includes a gel, wherein the gel is transparent when heated and opaque when the active ingredient and diluent has been volatized therefrom.

14. A volatile material dispenser, comprising:

a metallic tray having a bottom and side walls defining an open cavity containing a volatile material around which extends a peripheral lip, the tray having an outer surface covered with a laminate including a colored dye coated with a cast polypropylene layer; and a lid comprising:

a vapor permeable layer of biaxially oriented polypropylene film attached to the cast polypropylene layer at the peripheral lip to cover the cavity of the tray and permit release of vapors from the volatile material; and a removable impermeable cover laminate having a layer of foil joined to the vapor permeable layer attached to the tray and coated with a layer of polyethylene terephthalate, wherein the cover prevents release of vapors from the volatile material before removal.

* * * * *